United States Patent [19]
Dudzinski

[11] Patent Number: 4,594,455
[45] Date of Patent: Jun. 10, 1986

[54] AMINE COMPOSITIONS PRODUCED BY CATALYTIC ALKYLATION OF METHYLAMINE BY LONG CHAIN ALCOHOLS

[75] Inventor: Zdzislaw W. Dudzinski, Clifton, N.J.

[73] Assignee: Millmaster Onyx Group, Inc., New York, N.Y.

[21] Appl. No.: 593,025

[22] Filed: Mar. 23, 1984

[51] Int. Cl.$^4$ .................... C07C 87/06; C07C 85/06
[52] U.S. Cl. .................................. 564/463; 564/479; 564/480
[58] Field of Search ............... 564/480, 479, 478, 469, 564/463

[56] References Cited

U.S. PATENT DOCUMENTS 4,098,822 7/1978 Egan et al. ........................ 564/480
4,409,399 10/1983 Swift et al. ....................... 564/480

FOREIGN PATENT DOCUMENTS 0026528 6/1981 European Pat. Off.
2251826 4/1974 Fed. Rep. of Germany.

Primary Examiner—Paul F. Shaver
Attorney, Agent, or Firm—Arthur A. Jacobs

[57] ABSTRACT

A liquid phase catalytic alkylation of methylamine by long chain fatty alcohols, using as catalyst a mixture of compounds containing nickel, copper, and Group IIA metal, to provide mixtures of monoalkyl, dialkyl and trialkyl amines of preselected ratios, which, upon quaternization with methyl chloride, produce commercial mixtures of monoalkyl, dialkyl and trialkyl quaternary ammonium salts.

12 Claims, No Drawings

AMINE COMPOSITIONS PRODUCED BY CATALYTIC ALKYLATION OF METHYLAMINE BY LONG CHAIN ALCOHOLS

This invention relates to a process for producing a mixture of amines by the catalytic alkylation of methylamine with long chain fatty alcohols. It also relates to the quaternary ammonium salts which can be derived from these amines.

The catalytic alkylation of amines and ammonia by alcohols is well known and has been disclosed, inter alia, in U.S. Pat. No. 4,409,399. Compounds of nickel, copper and Group IIA metals are among the many catalysts which have been used for this purpose. The aforesaid U.S. Pat. No. 4,409,399 also discusses the shortcomings of all the prior art catalysts used in liquid phase alkylations of amines and discloses, in particular, a catalyst consisting of a mixture of unsupported copper oxide (or hydroxide), unsupported nickel oxide (or hydroxide), and a Group IIA metal oxide (or hydroxide).

U.S. Pat. No. 3,803,137 discloses a process for synthesizing a commercial mixture of primary, secondary and tertiary amines by the catalytic alkylation of ammonia with a mixture of primary aliphatic alcohols, the preferred catalyst being nickel on kieselguhr. The product has the fortuitous composition of 0–10 weight percent of primary alkylamine, 60–85 weight percent of secondary dialkylamine, and 5–25 weight percent of tertiary trialkylamine. The total conversion of alcohol to amine is at least 75%, preferably 85% by weight.

This mixture of amines is quaternized, preferably by methyl chloride and sodium hydroxide, to produce a mixture of quaternary salts whose composition parallels the composition of the mixture of amines with respect to molecular structures. Aqueous solutions of the mixture of these quaternary salts are described as having good freeze-thaw stability properties, and also good solubility properties because of their fortuitous proportions of mono-, di-, and tri-alkyl quaternary ammonium compounds.

Mixtures of quaternary ammonium compounds in which only long chain alkyl and methyl radicals are bonded to the quaternary nitrogen atom are used by many industries for many different purposes, such as textile softening, antistats, hair conditioning, sanitizing, disinfecting, controlling viscosity, emulsifying asphalt and oil, inhibiting corrosion, as additives in oil drilling muds, and in the manufacture of paints, printing inks and greases. With respect to the compositions of such quaternary salt mixtures, either in solid form or in aqueous solution, each industry has its own requirements, and even different companies within the same industry have their own requirements and specifications. The specifications depend on the purpose for which the quaternary salts are used and the manufacturers' unique requirements. A difference of only a few percent in one of the components may be sufficent to defeat the desired purpose.

The physical properties and specifications of the quaternary ammonium salt mixtures depend, to a very large extent, on the relative concentrations of monoalkyl trimethylammonium, dialkyl dimethylammonium, and trialkyl methylammonium salts in the mixture.

Since the mixtures of such quaternary ammonium salts are derived directly from the mixtures of amines by complete methylation, using a process which does not involve molecular rearrangements, the ratio of components in the mixture of quaternary salts obviously reflects the ratio of corresponding components in the mixture of amines. Therefore, in order to cater to the unique requirements of any single user of quaternary salt mixtures, it would appear to be highly desirable to have a process of producing amine mixtures which, by only minor adjustments, can produce various preselected ratios of amine components instead of depending on the fortuitous compositions of unique procedures. Such a process could be made to produce mixtures of amines of desired compositions which, upon quaternization with methyl chloride, for example, would lead to mixtures of quaternary ammonium salts whose compositions would fulfill the various specifications of individual users.

It is, therefore, an object of this invention, to find a process for producing a mixture of mono-, di-, and trialkylamines which, by slight alterations or minor adjustments, can yield varying but pre-selected approximate concentrations of these amines. It is a further object of this invention to quaternize these mixtures of amines so that the composition of the mixture of quaternary ammonium salts will meet the desired requirements and specifications of any individual user.

Other objects will be apparent from the following disclosure and claims.

In accordance with the present invention, it has been found that a mixture of (a) unsupported copper oxide, (b) unsupported Group IIA metal oxide or hydroxide, preferably where the metal is barium, calcium or magnesium and (c) nickel and/or nickel oxide on kieselguhr, acts as a surprisingly good catalyst for the alkylation of methylamine with alcohols. In all cases in which this catalyst mixture was used, conversion of alcohols to amines was practically 100%, the unreacted alcohol often comprising less than 1% of the product, often below even 0.25%.

The aforesaid U.S. Pat. No. 4,409,399 discloses that when nickel oxide or hydroxide is used together with copper oxide (or hydroxide) and barium oxide (or hydroxide) as the catalyst in the alkylation of methylamine, the product is virtually 100% dialkyl methylamine. It was, therefore, surprising to find that when nickel and/or nickel oxide on kieselguhr is substituted for unsupported nickel oxide (or hydroxide) considerable quantities of monoalkyl methylamine and trialkylamine were also produced, in addition to dialkyl methylamine.

It was even more surprising to discover that when the proportion of nickel and/or nickel oxide on kieselguhr was increased, relative to copper and Group II metal, in the catalytic mixture, the yield of trialkylamine in the product increased at the expense of the dialkylmethylamine.

In the above manner, merely by varying the proportion of supported nickel in the catalyst, it was possible to obtain a product that contained about 1% by weight of trialkylamine when the proportion of nickel is low, and a product that contains about 30% by weight of trialkylamine when the proportion of nickel is high. The amount of dialkylamine in the product can be varied from about 60% by weight when the ratio of nickel in the catalyst is high to about 90% by weight when the ratio of nickel is low.

The ratio of trialkylamine to dialkylmethylamine in the product is not changed appreciably by increasing or decreasing the amount of the catalyst. Therefore, increasing or decreasing the quantity of catalyst whose components are in the same proportion does not change appreciably the relative yields of trialkylamine and dialkylamine, but by changing the quantity of nickel in the catalyst mixture, the other components remaining unchanged, does change the composition of the product.

Increasing the amount of catalyst increased the reaction rate even though the composition of the product was not appreciably changed. Further, an increase in the reaction temperature between about 200° C. and about 230° C., also increased the reaction rate, but this, too, was accomplished without changing the composition of the product.

In the subsequent examples, the reaction temperature and the quantity of catalyst were chosen so that the reaction was complete within 8 hours.

As an exemplification of the present invention, a closed system was used which comprised an autoclave of 1 or 2 liter capacity fitted with an agitator, a thermometer, a condenser with a water trap and a gas inlet tube to direct entering gases beneath the surface of the liquid contents. The reactor was connected through the top of the condenser to a gas circulating system consisting successively of a gas circulating pump, a pressure gauge and pressure regulating device, a flow meter, and a gas mixing chamber of 20 liter capacity.

Methylamine and hydrogen gases in separate high-pressure cylinders were connected directly to the mixing chamber, the methylamine being routed through a valve which permitted the gas to be discharged into the chamber whenever the pressure in the circulating system fell below the pre-set level. By this means, the pressure in the system was kept constant. Since there is no net change in the quantity of hydrogen during the reaction, a drop in gas pressure, when it occurs, is due to the depletion of methylamine gas as it reacts, but this depletion may be immediately rectified by the introduction of an equivalent quantity of methylamine from the cylinder. Therefore, the pressure within the circulating system was kept constant and there was no change in the ratio of the two gases in the mixture during the reaction.

This type reaction is complete when no more water can be distilled out of the reaction mixture. This generally occurs between about 4 to 8 hours. However, before the reaction is halted, a small sample is withdrawn from the reaction mixture and analyzed by gas chromatography. If the same shows less than 1% of unreacted alcohol the reaction is halted, otherwise, it is permitted to continue until such time as the reaction mixture contains less than 1% by weight of unreacted alcohol.

The rate of flow of the gas mixture into the reaction chamber should be maintained at about 400 ml./min. to about 1000 ml./min. preferably about 600 ml./min. At flow rates of less than 400 ml./min., the reaction rate tends to decrease to a point where the reaction is not completed within an 8 hour period. At flow rates above 1 liter/min., the evolution of water vapor from the reaction mixture tends to be too great for complete condensation by the condenser so that water vapor is re-circulated with the gases. The flow rate in this instance was, therefore, maintained at about 600 ml./min. and the time for completion did not exceed about 8 hours.

The mixture of gases was pumped from the mixing chamber into the autoclave so that it entered beneath the surface of the liquid. Unreacted gases escaping from the reaction chamber through the top of the condenser were re-circulated through the mixing chamber.

As the unreacted gases escaped through the condenser, they carried with them water vapor, since water is a by-product of the reaction. The water vapor condensed and was collected in the water trap beneath the condenser.

The rate at which gas was circulated by the pump was monitored by the flow meter. The gas pressure was measured by the pressure gauge. The reaction temperature was measured by the thermometer which extended beneath the surface of the liquid reaction mixture.

In pilot plant operation, it was impractical to use a gas mixing chamber having 10 times the volume of the autoclave. Therefore, in pilot plan production, there were occasional ambient increases in pressure. These increases in pressure were relieved by bleeding off some of the gases.

Although a flow rate of 400–1000 ml/min. was used in the laboratory procedure described above, it is possible to accomodate different rates of flow for different capacity apparatus. Furthermore, a condenser of larger capacity might prevent the accumulation of water. In pilot plant operation such difficulty is overcome by using a condenser of extra large capacity.

The following example is illustrative of the invention:

EXAMPLE

The autoclave in the apparatus described above was charged with the liquid dodecyl alcohol to about half its volume and the heterogeneous catalyst was added. This catalyst comprised about 0.250% copper oxide based on the weight of the alcohol, about 0.125% of barium hydroxide based on the weight of the alcohol and about 0.063% nickel on kieselguhr based on the weight of the alcohol.

The nickel content of the latter component was provided by about 26% nickel oxide, about 26% reduced nickel and about 48% kieselguhr, the bulk density of this component being 28±3 lb./cubic foot and having a surface area of 100–200 square meters per gram. This component is a commercially available product called "G'49B Powder Catalyst" produced by United Catalyst Exports, Inc., Louisville, Ky.

The use of either reduced nickel on kieselguhr, or nickel oxide on kieselguhr, produced approximately similar ratios of amines in the product.

The entire system above the alcohol was evacuated, then filled with hydrogen gas to about 3 lbs. above atmospheric pressure.

While the liquid was agitated, hydrogen was circulated through the alcohol while the alcohol was slowly heated to 200° C., which took about 45 minutes. Then some hydrogen was bled from the system and replaced with methylamine gas so that about 4% by volume of the gaseous mixture was monomethylamine and 96% hydrogen. The mixture was maintained at 200° C. for about three hours.

The gas mixture of constant composition was re-circulated through the reaction mixture while the water of reaction was distilled out and trapped. The resulting product comprised a mixture of about 5.2% monalkylamine, about 84.7% dialkylmethylamine and about 4.8% trialkylamine.

It was found that when the gas flow rates were 400 ml./min. to 1000 ml./min., the rate at which the methylamine and hydrogen gas mixture was introduced into the reaction chamber had only a minor effect on the composition of the product. This was surprising inasmuch as methylamine is one of the stoichiometric reactants according to the equation $>N-H+HOR\rightarrow >N-R+H_2O$ where R is an organic alkyl radical.

On the other hand, at any rate of gas flow, the composition of the product mixture of amines was drastically changed by changes in the composition of the entering reactant gases. The higher the concentration of methylamine in the entering gases, the larger the quantity of monoalkylamine in the product at the expense of the dialkylmethylamine.

It was found that although some reasonable results were obtained when the concentration of methylamine in the entering gas was as high as 25% by volume, concentrations above 15% should generally be avoided because it was found that they often resulted in catalyst poisoning.

The present disclosure utilizes primary acylic, monohydric, branched or unbranched, saturated or unsaturated, fatty alcohols having from 8 to 20 carbon atoms where the terminal $-CH_2OH$ groups appear to be involved in the alkylation process. However, primary cyclic or polyhydric primary alcohols may also be used within the scope of the invention.

The pure alcohols that were used were n-octanol, n-decanol, n-dodecanol, n-tetradecanol, n-hexadecanol, and n-octadecanol, all primary acylic alcohols.

Under identical experimental conditions, mixtures of alcohols gave approximately the same distribution of monoalkylamines, dialkylmethylamines and trialkylamines in the products as was obtained using single alcohols, although there were cross alkylation products when mixtures of alcohols were used.

Illustrative of such alcohol mixtures utilized for the present invention was "Alfol 1618", a mixture of primary acylic unbranched monohydric fatty alcohols made by the Ziegler process. This material has the following composition, according to the number of carbon atoms per molecule:

| | |
|---|---|
| $C_{16}$ | 65.2% |
| $C_{18}$ | 34.8% |

"Neodol 25", a mixture of branched and unbranched primary acylic, monohydric alcohols made by the Oxo process was also used.

This mixture of alcohols has the following composition according to the number of carbon atoms per molecule:

| | |
|---|---|
| $C_{12}$ | 31.7% |
| $C_{13}$ | 37.5% |
| $C_{14}$ | 19.3% |
| $C_{15}$ | 11.5% |

The time taken to complete the reactions, using "Neodol 25", was about 25% more than the time used for the unbranched alcohols, and the slower reaction rate was attributed to the fact that "Neodol 25" contains about 20–30% of branched alcohols, predominately single methyl branching.

The following table discloses selected experimental results which were chosen to exemplify and illustrate the effect of different reaction conditions.

| Line Number | CuO | Ba(OH)$_2$ | Ni/K | T | t | % MMA | % M | % D | % Tr | Unreacted Alcohol |
|---|---|---|---|---|---|---|---|---|---|---|
| 1. | 0.25 | 0.125 | 0.063 | 220° | 3 | 4 | 5.2 | 84.7 | 4.8 | 0.0 |
| 2. | 0.50 | 0.250 | 0.125 | 220° | 6 | 4. | 4.8 | 87.7 | 3.2 | 0.5 |
| 3. | 1.0 | 0.50 | 0.25 | 210° | 2½ | 4 | 4.8 | 87.8 | 2.3 | 0.5 |
| 4. | 1.0 | 0.50 | 0.25 | 230° | 1½ | 4 | 6.0 | 86.5 | 2.7 | 0.0 |
| 5. | 1.0 | 0.50 | 0.25 | 220° | 2½ | 4 | 4.8 | 87.8 | 2.8 | 0.0 |
| 6. | 1.0 | 0.50 | 0.25 | 220° | 2 | 15 | 11.0 | 82.6 | 2.5 | 0.0 |
| 7. | 1.0 | 0.50 | 0.25 | 220° | 3½ | 25 | 20.7 | 70.5 | 1.4 | 0.7 |
| 8. | 0.25 | 0.125 | 0.063 | 220° | 6 | 4 | 5.2 | 84.7 | 4.8 | 0.0 |
| 9. | 0.25 | 0.125 | 0.25 | 220° | 4 | 4 | 4.9 | 76.1 | 9.1 | 0.0 |
| 10. | 0.25 | 0.125 | 1.00 | 220° | 2 | 4 | 3.0 | 65.6 | 26.7 | 0.4 |
| 11. | 0.25 | 0.125 | 0.063 | 220° | 6 | 4 | 5.2 | 84.7 | 4.8 | 0.5 |
| 12. | 0.25 | Ca(OH)$_2$ 0.125 | 0.063 | 220° | 6 | 4 | 10.5 | 80.6 | 4.3 | 0.0 |
| 13. | 0.25 | Mg(OH)$_2$ 0.125 | 0.063 | 220° | 7 | <u>4</u> | 13.5 | 74.4 | 4.3 | 3.4 |
| 14. | 0 | 0 | 4.0 | 220° | 2 | <u>4</u> | 5.7 | 52.2 | 36.7 | |

In the table, CuO repesents the percent of unsupported copper oxide powder in the catalyst, based on the weight of the alcohol; Ba(OH)$_2$, Ca(OH)$_2$, and Mg(OH)$_2$ represent the percent of unsupported Group IIA metal hydroxides in the catalyst, based on the weight of the alcohol; Ni/k represents the weight of the nickel catalyst (Ni and/or NiO on kieselguhr in the catalyst), based on the weight of the alcohol; T represents the temperature Celcius; t represents the time of the reaction in hours; % MMA represents the percent by volume of monomethylamine in the gas mixture entering the reaction chamber; % M represents the percent of monalkylamine in the product; % D represents the percent of dialkylmethylamine in the product; % Tr represents the percent of trialkylamine in the product: The total of all the pecentages does not add up to 100% because all of the alcohol reactants contained about 5% of unidentifiable impurities.

Lines 1 and 2 of the table show that the quantity of catalyst has very little, if any, effect on the composition of the product.

Lines 3 and 4 show that the effect of increasing the reaction temperature is to increase the reaction rate without altering the composition of the product to any appreciable extent.

Lines 5, 6, and 7 show that increasing the concentration of methylamine in the gas mixture which enters the reaction chamber serves to increase the yield of monoalkylamine in the reaction product, decreasing the yield of dialkylmethylamine, and decreasing very slightly the yield of trialkylamine.

Lines 8, 9, and 10 show that increasing the relative quantity of nickel on kieselguhr in the catalyst greatly increases the yield of trialkylamine in the product, and greatly reduces the yield of dialkylmethylamine, while the yield of monoalkylamine is also reduced to a minor extent.

Lines 11, 12, and 13 illustrate the differing effects of using three different Group IIA metal hydroxides in the catalyst. Barium hydroxide produces the highest yield of dialkylmethylamine and the lowest yield of monoalkylamine. Magnesium hydroxide produces the lowest yield of dialkylmethylamine and the highest yield of monoalkylamine. Calcium hydroxide produces the intermediate yields of both dialkylmethypamine and monoalkylamine. The yields of trialkylamine are approximately uniform for all three Group IIA hydroxides.

The weight of the copper oxide and Group IIA metal hydroxide together should be about 0.375% to 1.50%, based on the weight of the alcohol. Since the ratio of these catalyst components exerts more influence on the nature of the product than the quantity that is present, more than 1.50% of the mixture, based on the weight of the alcohol, is unnecessary. But quantities below 0.375%, based on weight of the alcohol, reduced the reaction rate to one that was unsatisfactorily slow.

When low concentrations of trialkylamine are sought in the product, the relative amount of nickel on kieselguhr must be low, so there should be a larger quantity of copper and Group IIA metal in the catalyst. However, when high concentrations of trialkylamine are required, there should be small quantities of copper and Group IIA metal so that the relative amount of nickel on kieselguhr may be made higher.

In order to reduce the impurities in the product, the ratio of copper oxide to Group IIA oxide or hydroxide in the catalyst had to be at least about 2 to 1 in the equipment used. A ratio which was much more favorable to Group IIA metal resulted in a catalyst which formed non-nitrogenous, high boiling esters in the product. For example, a catalyst containing copper oxide and barium hydroxide in 1:1 ratio produced about 3% of high boiling ester in the product; a ratio of 1:2 of these components yielded a product having about 5% of high boiling esters.

However, even though the ratio of at least 2 to 1 copper oxide to Group IIA oxide or hydroxide is preferable, especially when using equipment of the type described above, it is, nevertheless, possible to use other ratios which would result in the presence of a higher proportion of the high boiling esters and then extracting these esters. This would be a less satisfactory process but still feasible for some purposes. It might, furthermore, even be possible to use such products containing such high boiling esters for certain purposes, even though it would be, in general, a less satisfactory product than the substantially pure product obtained by using the preferable ratio of at least 2 to 1 set forth above.

The proportion of nickel and/or nickel oxide on kieselguhr in the catalyst must be chosen so that the required proportion of trialkylamine is produced.

When the catalyst contains about 15% nickel on kieselguhr, only about 5% of trialkylamine is produced in the product. However, about 75% of nickel on kieselguhr in the catalyst produced a product which contained over 25% of trialkylamine.

Because the present process produces very little secondary or primary amine, quaternization with methyl chloride requires very little caustic and yields very little sodium chloride by-product.

The invention claimed is:

1. A method of producing mixtures of amines by catalytic alkylation of methylamine which comprises reacting methylamine with a primary, acyclic, monohydric fatty alcohol, having 8 to 20 carbon atoms in the presence of a catalyst comprising a mixture of (a) unsupported copper oxide, (b) an unsupported Group IIA metal oxide or hydroxide and (c) either nickel, nickel oxide or a mixture of nickel and nickel oxide on kieselguhr.

2. The method of claim 1 wherein the alcohol is selected from the group consisting of n-octanol, n-decanol, n-dodecanol, n-tetradecanol, n-hexadecanol, n-octadecanol, and selected mixtures thereof.

3. The method of claim 1 wherein the Group IIA metal is selected from the group consisting of barium, calcium and magnesium.

4. The method of claim 1 wherein the combined weights of the copper oxide and the Group IIA metal oxide or hydroxide is between about 0.375% to 1.5% based on the weight of the alcohol.

5. The method of claim 1 wherein the ratio of copper oxide to the Group IIA oxide or hydroxide is at least about 2:1.

6. A product produced by the method of claim 1.

7. A product produced by the method of claim 2.

8. A product produced by the method of claim 3.

9. A product produced by the method of claim 4.

10. A product produced by the method of claim 5.

11. A method of producing selected mixtures of mono-, di- and tri-alkylamines which comprises reacting methylamine with a primary acyclic monohydric alcohol having 8 to 20 carbon atoms in the presence of a catalyst comprising a mixture of (a) unsupported copper oxide, (b) an unsupported Group IIA metal oxide or hydroxide and (c) either nickel, nickel oxide or a mixture of nickel and nickel oxide on kieselguhr, and varying the proportion of supported nickel in the catalyst to obtain varying proportions of dialkylmethylamine and trialkylamine in the resulting product.

12. The method of claim 11 wherein the proportion of the supported nickel is increased to increase the proportion of trialkylamine and is decreased to increase the proportion of dialkylmethylamine.

* * * * *